United States Patent
Lenz et al.

(10) Patent No.: US 9,320,683 B2
(45) Date of Patent: Apr. 26, 2016

(54) MONOLITHIC CERAMIC BODY WITH MIXED-OXIDE MARGINAL REGION AND METALLIC SURFACE, METHOD FOR PRODUCING SAME AND USE OF SAME

(75) Inventors: Sorin Lenz, Bad Reichenhall (DE); Christian Mahringer, Hallwang (AT); Günter Rübig, Wels (AT); Alexander Schreiner, Munich (DE)

(73) Assignee: CeramOss GmbH, Salzburg (AT)

( * ) Notice: Subject to any disclaimer, the term of this patent is extended or adjusted under 35 U.S.C. 154(b) by 80 days.

(21) Appl. No.: 13/878,410

(22) PCT Filed: Oct. 6, 2011

(86) PCT No.: PCT/EP2011/067492
§ 371 (c)(1),
(2), (4) Date: Apr. 8, 2013

(87) PCT Pub. No.: WO2012/045830
PCT Pub. Date: Apr. 12, 2012

(65) Prior Publication Data
US 2013/0199361 A1      Aug. 8, 2013

(30) Foreign Application Priority Data
Oct. 6, 2010   (EP) ..................................... 10186749

(51) Int. Cl.
*A61K 6/02*     (2006.01)
*F41H 5/02*     (2006.01)
(Continued)

(52) U.S. Cl.
CPC ............... *A61K 6/0205* (2013.01); *A61K 6/024* (2013.01); *A61K 6/0235* (2013.01); *A61L 31/022* (2013.01);
(Continued)

(58) Field of Classification Search
CPC ......................... C04B 41/0027; C04B 2235/75
See application file for complete search history.

(56) References Cited

U.S. PATENT DOCUMENTS 4,353,302 A    10/1982  Strandli et al.
4,532,149 A *   7/1985  McHargue .................... 427/527
(Continued)

FOREIGN PATENT DOCUMENTS

DE          10303351        9/2004
DE       102004041687        4/2006
(Continued)

OTHER PUBLICATIONS

I.Y. Guzman, A chemical technology of ceramics, 2003, 3 pages, OOO RIF "Stroymaterialy," Moscow, Russia.
(Continued)

*Primary Examiner* — David Sample
(74) *Attorney, Agent, or Firm* — Kolisch Hartwell, P.C.

(57) ABSTRACT

Monolithic ceramic bodies that have a mixed-oxide marginal region and a metallic surface, where the ceramic body includes an oxide of a first metal (I), while the mixed-oxide marginal region includes the oxide of the first metal (I) and the oxide of a further metal (II) having a high affinity for oxygen, and the metallic surface includes the further metal (II). The mixed oxide marginal region includes a continuous concentration gradient of the first metal (I), from 100% in the core to 0% in the transitional region to the metallic surface of the ceramic body, and a continuous concentration gradient of the further metal (II), starting from 0% in the core to 100% in the transitional region to the metallic surface of the ceramic body, where the oxygen concentration in the mixed-oxide marginal region remains constant, and the monolithic structure of the ceramic body has no phase boundaries.

21 Claims, 5 Drawing Sheets

(51) Int. Cl.
| | |
|---|---|
| *A61L 31/02* | (2006.01) |
| *C04B 35/488* | (2006.01) |
| *C04B 41/00* | (2006.01) |
| *C04B 41/52* | (2006.01) |
| *C04B 41/90* | (2006.01) |
| *C23C 14/48* | (2006.01) |
| *F41H 5/04* | (2006.01) |
| *C04B 111/00* | (2006.01) |

(52) U.S. Cl.
CPC .......... *A61L 31/026* (2013.01); *C04B 35/4885* (2013.01); *C04B 41/009* (2013.01); *C04B 41/52* (2013.01); *C04B 41/90* (2013.01); *C23C 14/48* (2013.01); *F41H 5/02* (2013.01); *F41H 5/0421* (2013.01); *A61L 2400/18* (2013.01); *C04B 2111/00405* (2013.01); *C04B 2111/00836* (2013.01); *C04B 2235/3232* (2013.01); *C04B 2235/404* (2013.01); *C04B 2235/614* (2013.01); *C04B 2235/75* (2013.01); *Y10T 428/1259* (2015.01); *Y10T 428/26* (2015.01)

(56) References Cited

U.S. PATENT DOCUMENTS

| | | | |
|---|---|---|---|
| 4,775,548 | A | 10/1988 | Lankford, Jr. |
| 4,892,849 | A * | 1/1990 | Lankford, Jr. ............... 501/97.1 |
| 5,028,306 | A * | 7/1991 | Davis et al. .............. 204/192.15 |
| 5,045,345 | A * | 9/1991 | Singer ........................ 427/527 |
| 5,340,058 | A | 8/1994 | Holl et al. |
| 5,476,691 | A | 12/1995 | Komvopoulos et al. |
| 5,546,365 | A | 8/1996 | Roth |
| 6,374,743 | B1 | 4/2002 | Hug et al. |
| 2001/0036530 | A1 | 11/2001 | Noda et al. |
| 2003/0175444 | A1 | 9/2003 | Huang et al. |
| 2005/0106534 | A1 | 5/2005 | Gahlert |
| 2006/0062912 | A1 | 3/2006 | Wortman et al. |

FOREIGN PATENT DOCUMENTS

| | | |
|---|---|---|
| EP | 0406021 | 1/1991 |
| EP | 0606566 | 7/1994 |
| EP | 0676761 | 10/1995 |
| EP | 0694918 | 1/1996 |
| EP | 0737974 | 10/1996 |
| EP | 2018879 | 1/2009 |
| GB | 2219886 | 12/1989 |
| JP | 1021054 | 1/1989 |
| JP | 02111680 | 4/1990 |
| WO | 9639943 | 12/1996 |
| WO | 03045268 | 6/2003 |

OTHER PUBLICATIONS

Ceramoss GmbH, Inquiry of the substantive examination of Russian Application No. 2013118171/03, Oct. 2, 2014, 13 pages.
Australian Patent Office, Patent Examination Report for Australian Application No. 2011311557, Oct. 10, 2013, 6 pages.
European Patent Office, Office Action for European Application No. 10186749.7, Dec. 30, 2011, 4 pages.
European Patent Office, Office Action for European Application No. 10186749.7, Aug. 2, 2012, 9 pages.
European Patent Office, Office Action for European Application No. 10186749.7, May 6, 2013, 5 pages.
European Patent Office, Office Action for European Application No. 10186749.7, Jul. 22, 2013, 4 pages.
M. Kononen and J. Kivilahti, Bonding of low-fusing dental porcelain to commercially pure titanium, 1994, 9 pages.
U. Tesch, K. Pabler, E. Mann, Untersuchungen zum Titan-Keramik-Verbund, Jan. 1993, 4 pages.
J. Tinschert, R. Marx, R. Gussone, Struktur von Keramiken fur die Titanverblendung, Jan. 1995, 1 page.
Jeremy L. Gilbert, David A. Covey, Eugene P. Lautenschlager, Bond characteristics of porcelain fused to milled titanium, Mar. 1994, 7 pages.
Ein Beitrag Von Geis-Gerstorfer J., Schille CH., Klein P., Geringere Oxidationsneigung unter Schutzgasatmosphare, Sep. 1994, 2 pages.
Lothar Wehnert, Andreas Moormann, Wolfgang B. Freesmeyer, Simulationsrechnungen zur Thermodynamik des konventionellen Titan-Keramik-Verbundes and zum Einflub des verbundverbessernden lonenimplantationsverfahrens, 1998, 11 pages.
European Patent Office, International Search Report for PCT/EP2011/067492, Jan. 13, 2012, 8 pages.
M. Kononen and J. Kivilahti, Fusing of Dental Ceramics to Titanium, 2001, 8 pages.
Japanese Patent Office, Office Action for Japanese Application No. 2013-532203, Aug. 11, 2014, 14 pages.
Andrea Bagno et al., Surface Treatments and roughness properties of Ti-based biomaterials, Journal of Materials Science: Materials in Medicine, Sep. 2004, 15 pages, Bd. 15, No. 9, Kluwer Academic Publishers, BO.
M. Franchi et al., Early detachment of titanium particles from various different surfaces of endosseous dental implants, May 2004, 8 pages, Biomaterials, Bd. 25, No. 12, Elsevier Science Publishers BV.
Karl-Heinz Frosch et al., Metallic Biomaterials in Skeletal Repair, Apr. 2006, 11 pages, European Journal of Trauma, Bd. 32, No. 2.
European Patent Office, European Search Report for European Application No. 08151711.2, Feb. 26, 2010, 11 pages.
European Patent Office, European Search Report for European Application No. 07014516.4, Dec. 13, 2007, 6 pages.

* cited by examiner

MONOLITHIC CERAMIC BODY WITH MIXED-OXIDE MARGINAL REGION AND METALLIC SURFACE, METHOD FOR PRODUCING SAME AND USE OF SAME

FIELD OF THE INVENTION

The present invention relates to a monolithic ceramic body, the production and use thereof. In particular the present invention relates to a monolithic ceramic body with a chemically altered marginal region of a mixed oxide, wherein the marginal region has a metallic surface. The ceramic body finds application in particular as implant.

BACKGROUND OF THE INVENTION

Implants generally serve as replacements for diseased or lost human or animal anatomical structures, such as teeth, joints, extremities etc. Preferably such implants should knit with the bone in the organism, to form a stable joint that is able to withstand loading long-term. Both titanium implants and ceramic implants are already available. Titanium implants are now well established in medicine, dentistry and veterinary medicine with over 30 years' experience of their use, whereas ceramic implants have only recently begun to be used in implantology. Owing to their excellent biocompatibility, bioinertness, corrosion resistance and their good physical properties, they have become well established in dentistry, mainly through use as implants, but they integrate with bone only poorly, or not at all.

Advantages of titanium are that it has very good osseointegration, i.e. it knits with bone, and it is not allergenic. The high affinity of titanium for oxygen leads to formation of a titanium oxide layer on the titanium implant surface, which leads to the advantageous properties. Bone knits with the titanium oxide layer. In order to maximize the contact surface between implant and bone as far as technically possible, the surface of the titanium implant is roughened. In this way osseointegration can be further improved. Today titanium is used for example for dental implants or in hip joints for titanium cups, which receive a ceramic insert, whereas in orthodontics, among other things anchoring implants made of titanium are used. The use of titanium in restorative dentistry became possible through further advances in casting technology and through the use of CAD/CAM and spark erosion techniques for making individual parts.

However, titanium has the following significant drawbacks, especially for dental implantology:

It has a dark, almost black color and, if it polished to a high gloss, a silvery color, so that the aesthetic appearance leaves much to be desired in the cervical zone of the tooth. Moreover, in dentistry, titanium implants cannot be cleaned, at the point where they emerge from the gum, with ultrasonic tips made of metal, as the material becomes scratched and roughness develops, which promotes increased dental plaque formation. Cleaning therefore requires special plastic tips.

Oxide ceramic (zirconium oxide ceramic, alumina, zirconia-alumina mixtures, etc.) is an extremely hard, smooth, biologically inert material, which is absolutely resistant to corrosion (acid, salts, body fluids). Moreover, owing to its hardness it is extremely abrasion-resistant, i.e. the surface can only be modified using diamond tools. Furthermore, the white color of the material offers—at least for dental implants—excellent aesthetic advantages in dentistry. These properties are already utilized in medicine, e.g. as stents for vessels in cardiology with a surface of ceramic so that there is no build-up of deposits of body cells. The aforementioned advantages are a disadvantage for the ceramic dental implants used in dentistry. Because the material is biologically inert, there is no or only insufficient osseointegration of the implant.

In order to combine the advantages of both materials, oxide ceramics and titanium, and eliminate the respective disadvantages as far as possible, two approaches have been adopted in recent times: implants made of a titanium body with a (partial) ceramic coating (facing) and implants made of a ceramic body with a titanium or titanium oxide coating. In the first approach, those regions of the titanium body that are not in contact with bone after implantation are provided with a ceramic coating. In the second approach, the regions of the ceramic body that are in contact with bone after implantation are coated with titanium or titanium oxide, so that better osseointegration can take place there. The regions of the implant that are not in contact with bone after implantation are left uncoated.

Owing to the material-specific properties of titanium, namely its low coefficient of thermal expansion, the extreme affinity of titanium for air and oxygen and the crystal lattice change at 882° C., the formerly usual metal-ceramic composite systems (metal main body with ceramic surface, facing ceramics) cannot be used, as it is not possible for a ceramic to be "faced" with metal.

Through reaction with ceramic constituents, an oxidative reaction layer already forms on the surface of the titanium body at temperatures of 750-800° C. At temperatures of almost 1000° C., such as are reached in the production of conventional ceramics, there would be extreme strengthening of the oxide layers and therefore the bond to the ceramic coating would be weakened. Moreover, owing to the crystal lattice change, stresses could be a problem, and could also have an effect of weakening the bond. Compared to other dental alloys, titanium has a particularly low coefficient of thermal expansion. The coefficients of thermal expansion of ceramic and metal must, however, be matched to one another, to prevent cracking and spalling of the ceramic, such as would occur on facing titanium with conventional ceramics. As is known by a person skilled in the art, metals expand with heat, whereas ceramics undergo shrinkage during sintering.

For a long time it was not possible to achieve satisfactory values of adhesion strength of titanium-ceramic systems. The lower adhesive bond between titanium and ceramic can be attributed both to the necessary adjustment of the coefficients of thermal expansion, and to the high affinity of titanium for oxygen, so that during firing of the ceramic, there is pronounced growth of the oxide layer. The brittleness of the oxide layer is regarded as the primary cause of the lower bonding values.

For this reason, special binders (adhesion promoters) were developed, which owing to their reducing properties should prevent the oxidation of titanium during firing of the ceramic (M. Kononen and J. Kivilahti, Bonding of low-fusing dental porcelain to commercially pure titanium, J Biomed Mater Res 1994, Vol. 28, No. 9, pages 1027-35; U. Tesch, K. Pässler and E. Mann, Investigations of the titanium-ceramic composite, Dent Lab, 1993, Vol. 41, p. 71-74). In order to compensate the high oxidation tendency of titanium and thus increase the values of adhesion strength of titanium-ceramic systems, special binders were developed, which loosen and envelop oxides present on the titanium surface and, with their glass-like nature, seal the surface against further oxidation (J. Tinschert, R. Marx and R. Gussone, Structure of ceramics for titanium facing, Dtsch Zahnärztl Z, 1995, Vol. 50, p. 31-4). Studies showed, however, that this procedure only led partially to the desired success. Gilbert et al. reported on an improvement of the adhesive bond (J. L. Gilbert, D. A. Covey and E. P. Lautenschlager, Bond characteristics of porcelain fused to milled titanium, Dent Mater, 1994, Vol. 10, No. 2, p. 134-140). However, Hung et al. could not find any significant improvement from using a binder (C. C. Hung, M. Okazaki and J. Takahashi, Effect of Bonding Agent on Strength of Pure Titanium-Porcelain System, J Dent Res, 1997, Vol. 76, p. 60).

A disadvantage of using binders is that another ceramic firing is required which, along with the increased time required, in particular causes additional thermal loading of the titanium. Aesthetic disadvantages caused by the binder also cannot be ruled out.

With the objective of decreasing the oxidation of titanium during firing, tests were undertaken for firing the ceramic under a protective gas atmosphere (J. Geis-Gerstorfer; Ch. Schille and P. Klein, Lower oxidation tendency under protective gas atmosphere, Dent Lab, 1994, Vol. 42, p. 1235-1236), but with only slight success, as mainly the ceramic constituents are made responsible as main supplier of oxygen for oxidation of the titanium (M. Kononen and J. Kivilahti, Fusing of dental ceramics titanium, J Dent Res, 2001, Vol. 80, No. 3, p. 848-854).

Another approach for increasing the strength of adhesion in a titanium-ceramic system is described in DE 10 2004 041 687 A1, according to which a layer of zirconium oxide is applied on a body of pure titanium by a CVD, PVD or plasma-immersion ion implantation and deposition technique, the ceramic for facing the titanium being burnt on without a binder. In this case the zirconium layer serves as adhesion promoter between the titanium body and the applied ceramic layer.

More recent approaches are based on coating a ceramic body with titanium, as it is known that titanium-coated ceramics show very good results with respect to osseointegration. WO 03/045268 A1 discloses, for example, a one-part tooth implant of a ceramic main body with a titanium coating.

However, it is also known that the strength of adhesion between the titanium coating and the ceramic also poses problems, as is known from US 2001/0036530 A1. US 2001/0036530 A1 describes an implant made of a composite material of a zirconium oxide ceramic with a first coating of titanium, a second coating also of titanium and optionally a third coating of hydroxyapatite. In this case, for better anchoring of the first coating and the associated desired better strength of adhesion, titanium ions are implanted in the ceramic by ion implantation. This can improve the strength of adhesion by 20% relative to known ceramic-titanium composite systems. The titanium-ceramic composite systems disclosed do not, however, have satisfactory properties. During investigation of the strength of adhesion, admittedly no cracking or spalling was observed, but the strength of adhesion, averaging 67 MPa, was not significantly above the strength of adhesion of 41 MPa achieved in the prior art. A similar approach was disclosed in EP 2 018 879 A1. However, once again satisfactory strength of adhesion could not be achieved. Thus, in the end, the effect that on loosening the layer, "blank" ceramic makes its appearance, could not be prevented. This effect is not only, but primarily unacceptable in implantology, as material failure has catastrophic consequences, because implants should remain in the body fault-free for decades and optimally for a lifetime.

There are applications, not only but primarily for implants, which require a very high strength of adhesion of the layer. Such applications are not only dental applications, but also other medical uses, such as bipolar prostheses (hemi-endoprostheses) for treating femoral neck fractures. The frequently used dual head prostheses consist of a head, a stem and a socket, consisting e.g. of polyethylene. This leads to the problem that the high mechanical loading causes wear of the polyethylene socket. This wear can lead to loss of sliding properties of the joint. Mainly the abrasion products lead to aseptic bone necrosis. This leads to technical failure of the dual head prosthesis and to consequent damage in the healthy tissue. The above remarks regarding the consequences of the abrasion products also apply to metal-metal pairs and metal-plastic pairs in orthopedic joint prostheses.

There is thus a need for materials for implants that fulfill all requirements in the most varied of applications for implants both from the chemical and the mechanical standpoint. Furthermore, they must have the capacity for osseointegration. There is in addition a need for a method with which these materials can be produced easily and economically in sufficient amounts.

DESCRIPTION OF THE INVENTION

The problem to be solved by the invention is therefore to provide a material that is biocompatible, undergoes osseointegration, and does not cause aseptic necroses by its abrasion products. Furthermore, this material should have the chemical and mechanical properties that are required in all applications of implants, and should be easy to produce. Another problem to be solved by the invention is to eliminate the problems of layer adhesion and to provide a method by which the material can be produced easily. The phase formations that arise in existing coatings should be avoided.

The problems to be solved by the invention were solved by providing a monolithic ceramic body as claimed in claim 1, a method of producing a monolithic ceramic body as claimed in claim 10 and the use thereof as claimed in claim 18. Preferred embodiments can be found in the dependent claims. The inventors recognized that the approach to solving the problems with new materials in general, and quite especially for implantology, involves eliminating the problems of layer adhesion, in order to ensure a decades-long residence time and serviceability in the body.

The present invention has in addition managed to combine the following advantages and effects:

Creation of an osseointegrating monolithic ceramic body with mixed-oxide marginal region and metallic surface with a structure similar to the structure of bone, with respect to softness, to the extent that microfractures of the osseous implant bed on loading can largely be prevented. As is known and described in the literature, under peak loads, particularly hard implant materials cause undesirable osseous microfractures of the bone in the implant bed—a problem for which no solution has been found hitherto, but which has now been solved with the present invention.

Monolithic ceramic bodies with mixed-oxide marginal region and metallic surface according to the invention eliminate the weak points of the ceramic main body not yet modified according to the invention, caused by microdefects of the surface (preformed weakened point). After modification according to the invention, this becomes more resistant to impact and thrust effects, and the splintering tendency is also eliminated as far as possible. A person skilled in the art is aware that conventional ceramics are very hard, but also very brittle, and on material failure they shatter into countless fragments.

Figure 1:
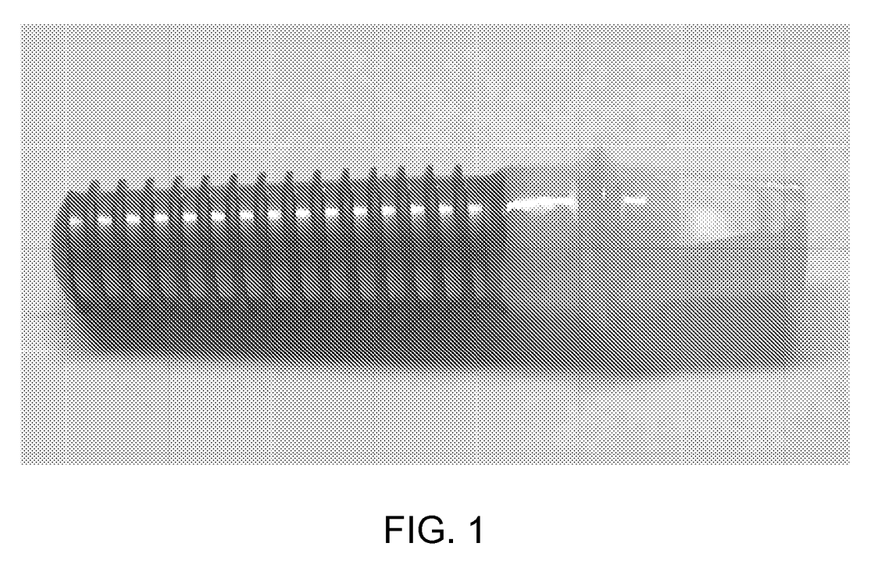
FIG. 1: shows a ceramic body according to the invention in the form of a one-part tooth implant. Only the threaded anchoring part for anchoring the implant in the bone has a zirconia-alumina-titanium mixed-oxide marginal region, with metallic surface of pure titanium. The core of the tooth implant consists of zirconia-alumina ceramic.
Figure 2:
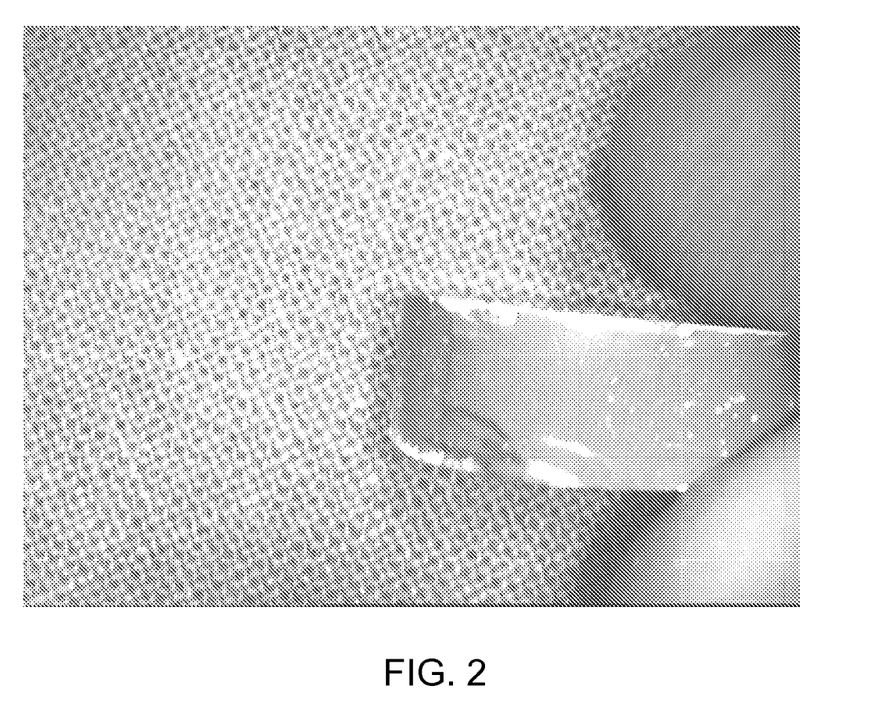
FIG. 2: shows a broken ceramic body according to the invention with core of zirconia-alumina ceramic, mixed-oxide marginal region of zirconia-alumina and titanium mixed oxide and metallic surface of pure titanium. The advantage according to the invention of absence of splintering tendency can clearly be seen.
Figure 3:
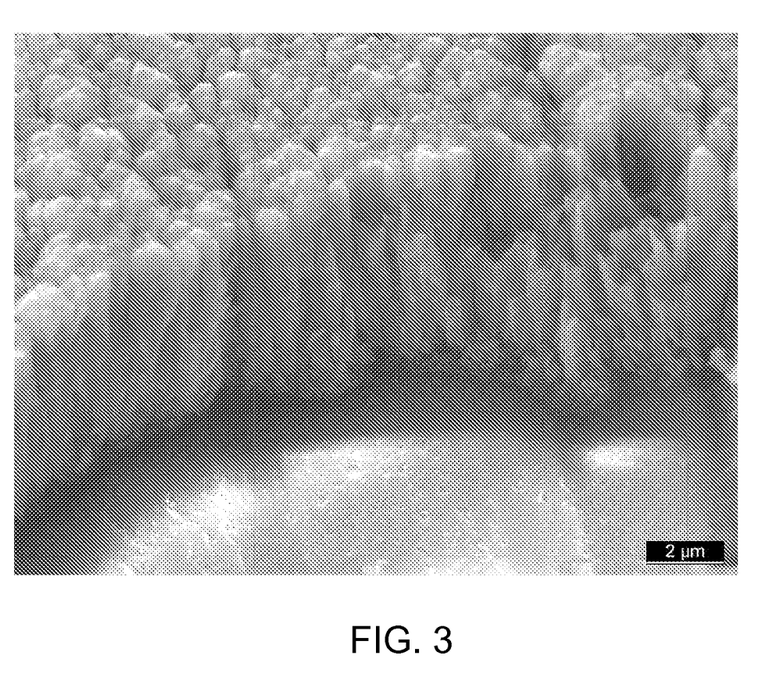
FIG. 3: shows the REM image of a fracture surface of a ceramic body according to the invention with core of alumina ceramic, mixed-oxide marginal region of alumina-titanium mixed oxide and metallic surface of pure titanium. In the background, the metallic surface can be seen, which in this case has a "soft" bone-like structure and should prevent microfractures in the implant bed. The blank area in the foreground is the mixed-oxide marginal region and the alumina core.
Figure 4:
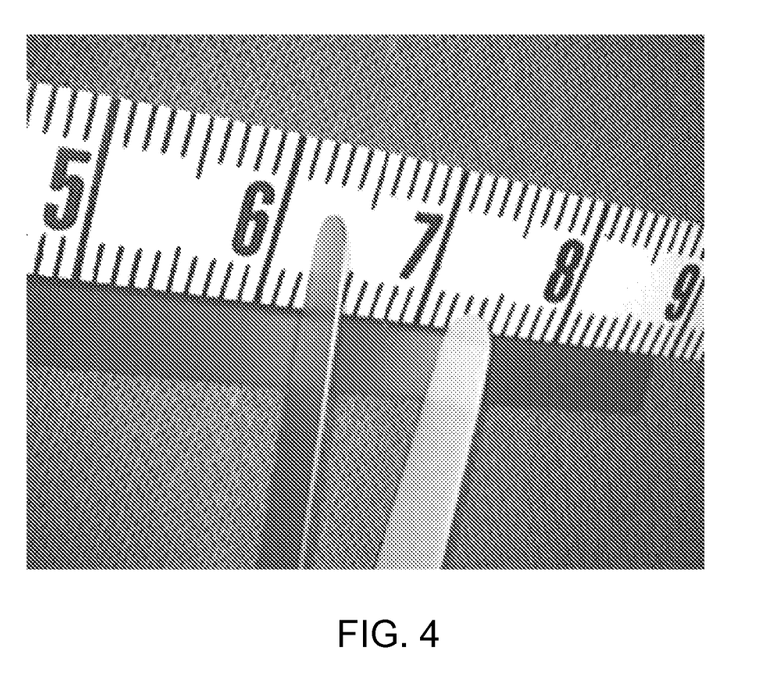
FIG. 4: shows two approx. 1 mm thick oxide ceramic lamellae, on the left according to the invention with metallic surface of titanium and on the right, conventional without titanium surface. The ceramic lamella according to the invention has a core of zirconia-alumina ceramic and a mixed-oxide marginal region of zirconia-alumina-titanium mixed oxide and a metallic surface of pure titanium.
Figure 5A:
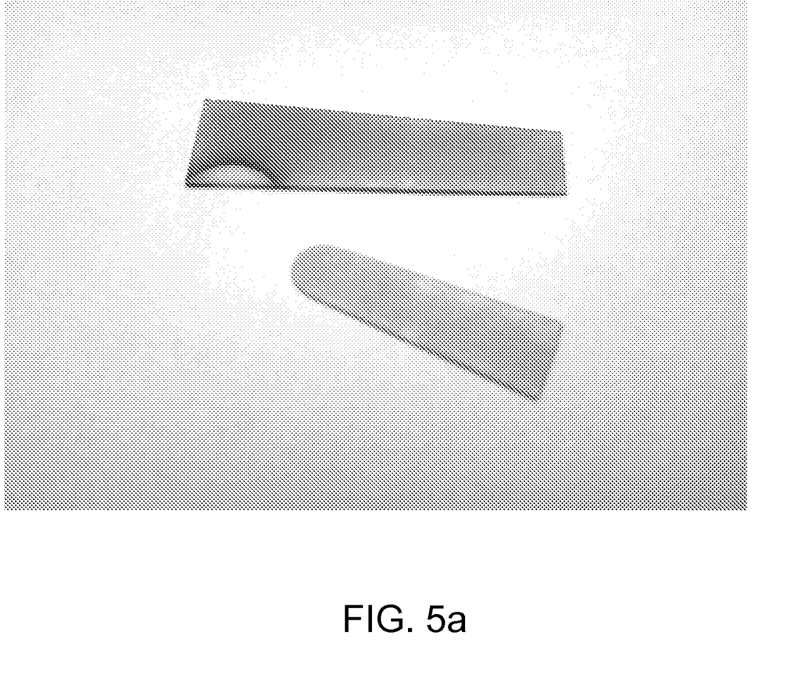
FIGS. 5a, 5b: show in each case two defined fragments of the ceramic lamella according to the invention from FIG. 4. Splintering into many separate parts did not occur in the fracture test. During bending as far as fracture, there was also no spalling tendency of the surface, as usually occurs with conventional coatings.
Figure 5B:
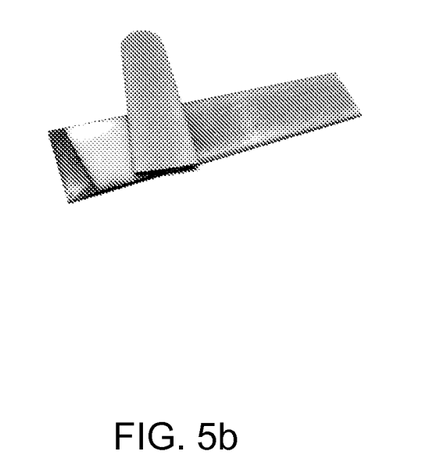
Figure 6:
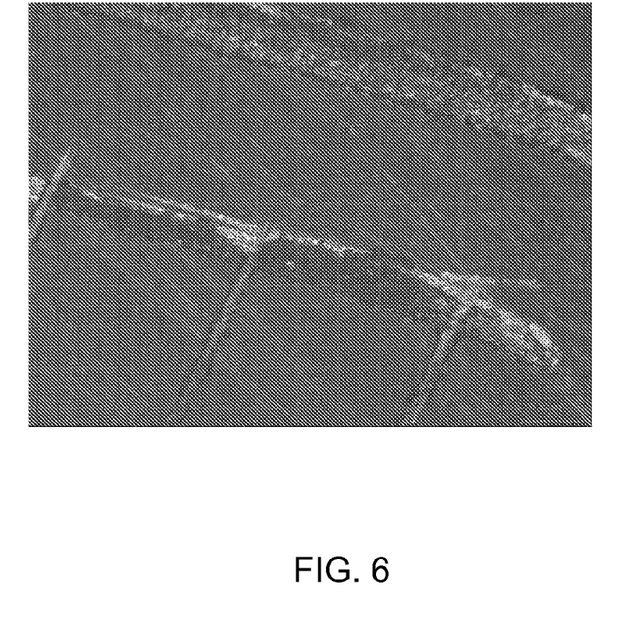
FIG. 6: shows a square-cut adhesion test of a ceramic body according to the invention with core of aluminum oxide ceramic, mixed-oxide marginal region of aluminum oxide-titanium mixed oxide and metallic surface of pure titanium. No spalling tendency is seen. The ceramic forming the core is not loose.
Figure 7:
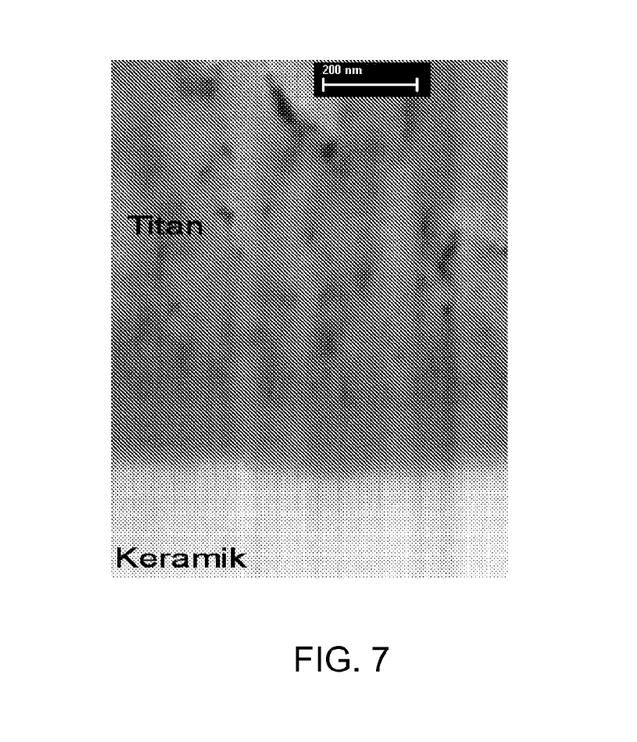
FIG. 7: shows the REM cross-sectional image (high magnification) of a ceramic body according to the invention with core of zirconia-alumina ceramic, mixed-oxide marginal region of zirconia-alumina-titanium mixed oxide and metallic surface of pure titanium. The ceramic core is the light region at the bottom. Above this there is the grayish mixed-oxide marginal region (approx. 700 atomic layers), in which the nonuniformly dark gray to black surface of pure titanium is located.
Figure 8:
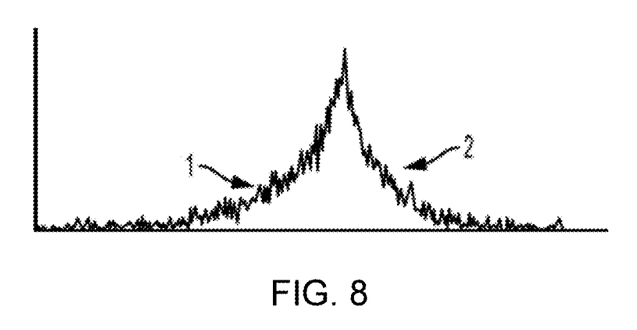
Figure 9:
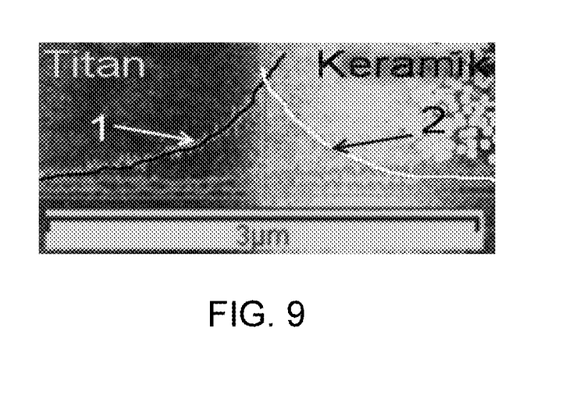
FIG. 9: shows the EDX diagram according to FIG. 8, which is projected into the REM cross-sectional image according to FIG. 7 at the corresponding point. What was said regarding FIG. 8 applies similarly.

Investigation of monolithic ceramic bodies according to the invention in the form of ceramic lamellae with a thickness of approx. 1 mm found that these bodies were much more flexible than ceramic bodies not according to the invention, and on fracture they do not splinter like conventional ceramic lamellae into countless fragments, but break into two pieces with a defined break point (see FIGS. 4, 5a and 5b).

Monolithic ceramic bodies according to the invention have much higher impact and compressive strength through absorption and uniform redistribution of pressure, as the mixed-oxide marginal region and the metallic surface are much more elastic than ceramic and are thus able to prevent microcracking. This means that mechanical overloading to fracture occurs much later, because, as is known from the literature, microcracks on the surface of ceramic move rapidly through the ceramic and cause it to splinter. In the human body, such splintering comes close to a catastrophe, as all the splinters must be removed, which is not always completely successful. Any splinters remaining in the human body then cause persistent complaints. This problem is eliminated as far as technically feasible by the use of the implants according to the invention and is avoided as far as possible.

Monolithic ceramic bodies according to the invention behave like metals on the surface. Therefore further desired modification or machining of the surface can be carried out economically, as already known from metal processing.

The particular advantage of the monolithic ceramic body according to the invention with mixed-oxide marginal region and metallic surface consists of the cumulative solution of many problems not solved previously (listed above). Furthermore, a cumulative substantial improvement of the ceramic properties is achieved, relative to conventional ceramic bodies. This result is achieved without loss of the desirable and required positive properties of conventional ceramic bodies (hardness, abrasion resistance, etc.), as production of the monolithic ceramic body according to the invention with mixed-oxide marginal region and metallic surface takes place in the low temperature range. In addition to the solutions of problems already presented, another advantage is achieved when the monolithic ceramic body according to the invention with mixed-oxide marginal region and metallic surface is used as protective armour plating. The surface then serves as a lubricant (slip agent), e.g. when there are impinging projectiles.

The ceramic body according to the invention consists of the oxide of a first metal (I) with a mixed-oxide marginal region (metal I+II) and a metallic surface of the metal (II). The mixed-oxide marginal region comprises the oxide of the first metal (I) and the oxide of the other metal (II), which has a high affinity for oxygen. The inventors found, surprisingly, that the mixed-oxide marginal region has a continuous, uniform concentration gradient of the first metal (I), starting from 100% in the core to 0% in the transition region to the metallic surface of the ceramic body, relative to the total metal content (I+II), and a continuous, uniform concentration gradient of the other metal (II), starting from 0% in the core to 100% in the transition region to the metallic surface of the ceramic body, relative to the total metal content (I+II). In contrast, the oxygen concentration remains constant in the mixed-oxide marginal region. The surface of the monolithic body according to the invention is metallic (metal II), and therefore is not a (metallic) coating.

Manufacture according to the invention produces a monolithic ceramic body with mixed-oxide marginal region and metallic surface. The phase boundaries that are clearly discernible with a coating are nonexistent with the ceramic body according to the invention, as it is not a coating, but a monolithic structure resulting from a thermochemical reaction.

Phase boundaries (a typical feature of coatings) are not to be found in the transition region of metal (I) to the mixed-oxide marginal region of metals (I+II), or in the mixed-oxide marginal region itself, or in the transition region of the mixed-oxide marginal region (metal I+II) to the metal surface (metal II) of the ceramic body. "Without phase boundaries" means, in the sense of the present invention, a concentration gradient for which there are no material boundaries.

"Region" in the sense of the invention means, as distinct from the term "layer", that the chemical composition within the "region" varies, also within an atomic layer of the region. In contrast, a "layer" is characterized in that it has phase boundaries and the whole layer has a defined chemical composition, which is the same across the layer.

"Ceramic" in the sense of the invention comprises, in addition to the raw materials that are used for the production of ceramic products, and their processing to the actual ceramic, also the objects themselves, formed from ceramics and fired, which are used as components, protective armour plating for civil and military purposes—for persons, vehicles, buildings (personal body protection, armour plating of buildings, armour plating for motor vehicles, ships, submarines, aircraft, rockets, etc.), utensils and decorative objects or tools.

"Metal (I)" and "metal (II)" in the sense of the invention does not mean the oxidation state of the metals. The numbering (I) and (II) serves for differentiating the metal that is a constituent of the ceramic, for which the designation "first metal" or "metal (I)" is used. In the case of the metal that is used for forming the mixed-oxide marginal region, the designation "the other metal" or "metal (II)" is used for this. The terms "first metal" and "metal (I)" and "the other metal" and "metal (II)" are used synonymously.

"Marginal region" in the sense of the invention is the region of the ceramic body according to the invention that begins beneath its metallic surface and extends toward the interior of the ceramic body as far as its core of the oxide of the first metal (I).

"Marginal zone" in the sense of the invention is the region of the ceramic body according to the invention that is formed by the metallic surface and the underlying marginal region.

"Unfinished ceramic body" in the sense of the present application is a ceramic body that has not yet been modified according to the invention.

"Marginal region of the unfinished ceramic body" is the region of the unfinished ceramic body that extends starting from its external surface toward the interior of the unfinished ceramic body.

The advantages achieved with the invention are to be considered in particular that the ceramic body according to the invention can no longer be called a composite material, i.e. a ceramic body with a metal coating (since phase boundaries as a characterizing feature of a coating are no longer present). Instead it is a monolithic ceramic body with mixed-oxide marginal region and metallic surface. Accordingly, the terms "layer adhesion" and strength of adhesion are no longer applicable. Rather it is a region of the ceramic body that has been modified thermochemically.

In conventional composite systems, three groups of forces between the metal and the facing ceramic result in production of the composite, namely mechanical, adhesive and chemical forces. The mechanical forces develop through the shrinking-on of a ceramic onto the metal structure during the sintering process. The coefficients of thermal expansion and the retention, i.e. the mechanical keying of the composite partners together, are responsible for these forces. The intermolecular forces of attraction (Van der Waals forces) are responsible for the adhesion between the composite partners. These include in particular dipole interactions and hydrogen bridge bonds. The formation of a mixed oxide leads to the chemical force. The surface of the metals to be coated with a ceramic, to a varying extent depending on the type of metal, does not consist of pure metal but of metal oxide. These metal oxides are joined retentively and adhesively to the metal structure. The chemical bonding between the metal structure and the ceramic occurs on the oxidized surface of the metal. Firing of the ceramic produces mutual bonds between the metal oxide layer and the ceramic main body. So-called oxygen bridges are formed. However, what is decisive in the conventional composite systems is not only what force acts to what extent, but also the strength of adhesion of the metal oxide layer on the metal. Regardless of which force predominates in the particular composite, the composite system consists of many different layers.

The inventors found, with the monolithic ceramic body according to the invention with mixed-oxide marginal region and metallic surface, that the ceramic body does not have a layer structure up to the surface (there are no phase boundaries). In contrast to coating, there are no thin layers with identical chemical composition and therefore layers with different chemical composition on top of one another, which adhere to one another, instead a complex system is obtained, in which the metal ions (II) react with the oxygen of the ceramic (I), so that a new chemical compound is formed, consisting of metal ions (I), metal ions (II) and oxygen. The inventors presume that a (thermo-) chemical reaction takes place between the oxygen atoms of the ceramic (oxide of metal I) as solid body and the metal ions (II), so that a region is formed in which the marginal region of the ceramic body is modified chemically continuously, as far as an external metal surface, without resulting as usual only in "incorporation" of the metal ions (II) into the lattice of the ceramic material (in this case phase boundaries are present), by which the lattice would be disturbed and ions would be expelled from the ceramic lattice.

Rather it is observed that the concentration of metal (II) increases continuously, starting from 0% in the core of the ceramic to 100% in the transition region to the metallic surface, relative to the total metal content, and the concentration of metal (I) decreases continuously starting from 100% in the core of the ceramic to 0% in the transition region to the metallic surface, relative to the total content. Surprisingly, the oxygen concentration in the mixed-oxide marginal region remains constant. Therefore the chemical composition of the ceramic body varies from the interior of the body to its surface, wherein in the marginal region there is formation of a mixed oxide of metal (I) and metal (II), which finally ends in a metallic surface of metal (II) with a 100% concentration of metal (II).

This has the advantage that there is no formation of layers (phases, phase boundaries) and therefore no longer any limitation of the strength of adhesion. All attempts to bring about material failure of the surface of the monolith according to the invention (layer adhesion tests with superglue) ended in failure of the superglue, without exposed ceramic. The monolith according to the invention remained intact. The problems of layer adhesion are therefore no longer applicable, and nor are attempts to improve the layer adhesion. These problems have been solved according to the invention. Solution of the other problems mentioned above has already been mentioned.

Consequently it is not a coating. There can no longer be any discussion of layer adhesion or strength of adhesion. The ceramic body has the advantageous properties of a metal-coated ceramic and overcomes the disadvantages of strength of adhesion of conventional metal-ceramic composites. The chemical modification of the marginal region of the ceramic creates a monolith, with an inseparable chemical bond between the ceramic (oxide of metal I), the mixed-oxide marginal region based on metals (I) and (II) and the metallic surface formed of metal (II).

According to the invention, the ceramic is an oxide ceramic, consisting of the oxide of a metal (I), wherein metal (I) comprises zirconium, aluminum, yttrium, hafnium, silicon, magnesium, cerium, other metal oxides or metallic glass or mixtures thereof. Preferably, metal (I) is zirconium or comprises zirconium. Zirconium oxide and alumina are white and therefore their use is preferred in dentistry.

The ceramic body can be preformed before the thermochemical formation of the mixed-oxide marginal region and before sintering. This means that a green ceramic is formed into a desired shape and is then sintered. This has the advantage that the green ceramic is relatively soft and can be molded easily, compared with the hard ceramic after sintering. Accordingly, individualized or tailor-made implants can be produced at comparatively low cost, e.g. by 3D reconstruction. This also makes the production of complex anatomical structures possible.

"Green ceramic" in the sense of this invention means ceramic material before the final sintering process.

The green ceramic can be produced, molded and processed by methods that are known by a person skilled in the art, such as hot isostatic pressing, pressing, turning, grinding, boring, polishing or machining, etc., wherein the processes can be manual or can be numerically controlled by computer.

The preformed ceramic can be treated mechanically or physically before or after sintering, for example to increase the surface area. The increased surface area improves osseointegration, when the monolithic ceramic body according to the invention with mixed-oxide marginal region and metallic surface is used as implant. The chemical, mechanical or physical treatment is preferably carried out on the green ceramic, because then, because the material is soft, the treatment can be carried out faster, more easily and less expensively than after sintering, but it can also take place after sintering.

"Mechanical treatment" in the sense of the invention comprises in particular grinding, sandblasting or blasting with a water jet, and all other methods known by a person skilled in the art. "Physical treatment" in the sense of the invention comprises in particular irradiation with a laser beam, and all other methods known by a person skilled in the art.

Furthermore, the green ceramic can also be treated chemically, e.g. etching with an acid or an acid mixture. The acid or the acid mixture can be selected from phosphoric acid, sulfuric acid, hydrochloric acid, hydrofluoric acid, nitric acid, nitric acid/hydrochloric acid mixture, such as aqua regia, or hydrochloric acid/sulfuric acid mixture. The same also applies to sintered ceramic, which can be treated with suitable acids or acid mixture (all suitable methods known by a person skilled in the art).

The metal (II) for forming the mixed-oxide marginal region based on metals (I) and (II) and the metallic surface of metal (II) is according to the invention a metal with high affinity for oxygen and is selected from titanium, niobium, tantalum and compounds and alloys thereof. Other metals with affinity for oxygen are not excluded.

Metal (II) is preferably elemental titanium, a titanium compound or a titanium alloy. In some embodiments the titanium compound can be a compound of titanium with elements of the 14th (e.g. C, Si, Ge, Sn, Pb), 15th (e.g. N, P, As, Sb, Bi) or 16th (e.g. O, S, Se, Te, Po) group of the periodic table or a mixture thereof. Elemental titanium is especially preferred as metal (II), and 100% pure titanium is quite especially preferred.

The thickness of the mixed-oxide marginal region is determined on the one hand by the depth of penetration of the metal ions (II) during implantation according to the invention, and on the other hand by their diffusion and by the thermochemical reaction in the ceramic body. The desired chemical reaction takes place here, which represents the essential distinguishing feature relative to the conventional ion implantation, in which there is only "incorporation" of metal ions into the lattice of the ceramic material (phase boundaries are present). The reactive marginal region has on average a thickness of about 700 atomic layers, which corresponds to about 140 nanometers. According to the invention the thickness is at least 500 atomic layers, but can also be less, but only so far less, such that no weakening of the monolith occurs. At least 700 atomic layers and especially preferably more than 700 atomic layers are preferred.

A marginal region with a thickness greater than 700 atomic layers is difficult to produce, is particularly expensive and does not give any evident advantage or further improvements with respect to the applications of the monolithic ceramic body with mixed-oxide marginal region and metallic surface and with respect to the material advantages achieved.

The thickness of the marginal zone from the external metal surface of metal (II) to metal (I) inside the ceramic body (including the mixed-oxide marginal region based on metals (I)+(II)) is 6-8 micrometers in section. This marginal zone can have a thickness from 0.05 micrometer (smaller thickness is expressly not excluded), up to several millimeters (larger thickness is expressly not excluded). Thicknesses between 0.05 and 80 micrometers are preferred, and between 5 and 20 micrometers are quite especially preferred.

In further embodiments according to the invention the ceramic body can, if necessary, be provided with one or more coatings of metal (II) and/or one or more coatings of a biocompatible and/or bioactive material, especially with a microporous titanium coating.

One possibility for "bone-friendly" surface configuration is at present coating with calcium phosphate (also beta-tricalcium phosphate, etc.), which is regarded as bioactive (osseoactive), i.e. it promotes the development of bone tissue and makes available inorganic components for growth. Hydroxyapatite coating has found wide application in implantology. The chemical composition of the coating material, its strength of adhesion on the carrier substance, the coating thickness and resorptive processes within the coating influence the reaction of the bone tissue and therefore the clinical usability of coated implants.

The biocompatible/bioactive material can moreover be selected from antibiotics, growth factors, peptides, fibronectin and anti-inflammatory agents. Other biocompatible/bioactive materials known by a person skilled in the art can be used, and are expressly not excluded.

The following may be mentioned for example as antibiotics: amikacin, gentamicin, kanamycin, neomycin, netilmicin, paromomycin, streptomycin, tobramycin, cephalosporins, fluoroquinolone antibiotics, azithromycin, erythromycin, clarithromycin, dirithromycin, roxithromycin, telithromycin, penicillins, ampicillin, sulfonamides, tetracyclines, clindamycin, metronidazole and vancomycin, etc.

As growth factors, mention may for example be made of transforming growth factor beta (TGF-β), granulocyte colony stimulating factor (G-CSF), granulocyte-macrophage colony stimulating factor (GM-CSF), nerve growth factor (NGF), neurotrophin, platelet derived growth factor (PDGF), erythropoietin (EPO), thrombopoietin (TPO), myostatin (GDF-8), growth differentiation factor-9 (GDF-9), acidic fibroblast growth factor (aFGF or FGF-1), basic fibroblast growth factor (bFGF or FGF-2), epidermal growth factor (EGF), hepatocyte growth factor (HGF), insulin-like growth factors (IGFs) and bone morphogenetic proteins (BMPs), etc.

As anti-inflammatory agents, we may mention for example glucocorticoids, corticosteroids and nonsteroidal anti-inflammatory drugs (e.g. ibuprofen, aspirin and naproxen, etc.).

A peptide can for example be a bioactive peptide such as the RGD sequence.

In a special embodiment according to the invention the biocompatible material comprises a bioactive surface coating of osteochondral/osseous stem cells or chondral stem cells or a mixture thereof. The stem cells improve the osseointegration of the monolithic ceramic body with mixed-oxide marginal region and metallic surface coated therewith.

It has proved especially advantageous if the surface of the monolithic ceramic body with mixed-oxide marginal region and metallic surface is treated chemically, mechanically or physically to increase the surface area before coating with a biocompatible material.

Monolithic ceramic bodies with mixed-oxide marginal region and metallic surface can be produced easily with the method according to the invention.

The method according to the invention for producing a monolithic ceramic body with a mixed-oxide marginal region and metallic surface comprises the following steps, which are carried out in a thermochemical reaction chamber on an unfinished ceramic body with a marginal region:
   (a) evacuating the reaction chamber to a negative pressure of $10^{-3}$ mbar or less,
   (b) activating the marginal region of the unfinished ceramic body, and
   (c) starting the thermochemical treatment of the marginal region of the unfinished ceramic body.

In step (a), a high-vacuum between $10^{-3}$ mbar and $10^{-7}$ mbar is preferred. A vacuum that is as close as possible to the vacuum of outer space is especially preferred.

Evacuation most preferably takes place hours before the start of the process, in order to remove disturbing components and contaminants from the reaction chamber, and to make it possible for the intended thermochemical reaction on a solid body to take place at all. Another advantage of high vacuum is that the free path of the metal ions (II) is relatively high, before there is collision with other particles, such as contaminants or noble gas atoms or ions, which can cause the metal ions (II) to lose energy. Owing to the high vacuum, there is no energy loss of the titanium ions through friction in their motion to the ceramic.

An important aspect of the invention is that the reaction chamber is essentially free from compounds, especially oxygen, with which the other metal ions (II) can react. "Compounds" in the sense of the invention means chemical compounds and atoms/ions.

If such compounds are present in the reaction chamber, the high-energy metal ions (II) can react with these compounds, especially oxygen, which leads to the formation of undesirable compounds, such as titanium oxide, and they are no longer available for forming the mixed-oxide marginal region. The compounds formed can, if their energy is still sufficient, be implanted farther into the marginal region of the ceramic body, which can lead to the disadvantages associated with conventional ion implantation, such as disturbance of the ceramic lattice. Moreover, the undesirable compounds may be deposited as a surface coating on the ceramic body and thus form a disturbing layer, which in its turn can prevent formation of the mixed-oxide marginal region.

It is therefore necessary to ensure that the metal ions (II) impinge unimpeded on the ceramic body, i.e. without reacting on the path between target and ceramic body, so as to be able to react with the latter thermochemically and uniformly.

In step (b) of the method according to the invention, the marginal region of the unfinished ceramic body is activated. More precisely, the atoms in the marginal region of the ceramic body that has not yet been modified according to the invention are shifted to an energetically excited state. This is necessary to make it possible for the mixed-oxide marginal region according to the invention to form.

For activation of the marginal region, the methods known from the prior art can be employed according to the invention, such as flame treatment with a burner, plasma treatment, corona treatment. A plasma technique is preferably used for activation of the marginal region.

Activation of the marginal region by plasma treatment has the advantage that, among other things, the surface of the ceramic substrate is purified first, i.e. contaminants are removed. A plasma treatment is preferred in which, along with activation of the marginal region of the ceramic body, in addition the marginal region is initially etched and activated in the sense of plasma-chemical activation, to increase the reaction area and create increased readiness for the desired thermochemical reaction between metal (I) and metal (II). The reactivity of metal (I) is increased as a result.

The activation of the marginal region preferably takes place with a plasma produced by an electrical gas discharge under high vacuum, wherein the energy and the duration of action of the plasma on the surface of the ceramic body are selected so that the atoms of the marginal region are activated in such a way that a chemical reaction becomes possible at all and can take place in the marginal region of the ceramic body.

Preferably, prior to activation of the marginal region of the ceramic body, the contaminants released are outgassed. The outgassing preferably takes place for several hours, but can also be much shorter or longer, at a temperature from 25° C. to 400° C., preferably below 350° C., wherein other temperatures are not excluded, and at a pressure of preferably $10^{-7}$ to $10^{-3}$ mbar, wherein the outgassings are pumped out of the reaction chamber continuously by means of vacuum pumps.

Then, for activation, the marginal region of the material or component is bombarded with ions and/or electrons, which are produced by an electrical gas discharge under high vacuum. The pressure in the reaction chamber is in the range between $10^{-5}$ and $10^{-3}$ mbar, preferably $10^{-7}$ and $10^{-3}$ mbar, especially preferably in the region of the vacuum of outer space. At these pressures, the energy of the plasma particles, which is correlated with the mean free path, is large enough for the atoms present in the marginal region of the ceramic body to be excited energetically in such a way that chemical reactions become possible in the marginal region of the ceramic body, which are not possible under other conditions.

Plasma activation is carried out by methods that are known by a person skilled in the art.

Noble gases are used as gases for the gas discharge. The noble gas is selected from argon, neon, krypton and xenon, wherein argon is preferred. Other suitable noble gases are not excluded.

It is therefore necessary to ensure that the metal ions (II) impinge on the ceramic body unimpeded, i.e. without reacting on the path between target and ceramic body, in order to be able to react with the latter thermochemically and uniformly.

As an alternative to applying a high vacuum to the reaction chamber, methods and/or devices are conceivable, with which the disturbing contaminants, especially oxygen, can be removed from the reaction chamber atmosphere, to achieve the effect according to the invention.

In step (c), the marginal region of the unfinished ceramic body is submitted to a thermochemical treatment. This alters the chemical composition of the marginal region of the ceramic body.

Thermochemical treatment in the sense of this invention is a thermal treatment that is applied to a material (metal (I)) for the purpose of altering the chemical composition of the material by mass transfer with the medium supplied (metal (II)). In general, in thermochemical treatment, metallic or nonmetallic elements diffuse into the surface of a material. In the course of thermochemical treatment, either a diffusion region or a connecting region with diffusion region beneath it can be formed. Within a diffusion region, the content of the diffused element (metal II) decreases continuously, uniformly, gradually toward the core and the content of the reacting element (metal I) decreases continuously, uniformly, gradually toward the surface; in contrast, in the case of a connecting region the concentration decrease is as a rule very steep.

According to the invention, the thermochemical reaction of the ceramic body is started with the assistance of ion implantation. This means that in a first stage, metal (II) ions are implanted in the marginal region of the unfinished ceramic body (metal (I)), from where they can diffuse farther into the ceramic body and can react. This results in formation of a connecting region, namely in the region of ion implantation, and a diffusion region beneath it. Owing to the high energy of the metal (II) ions and the activation of the marginal region carried out in step (b), in the second stage the metal (II) ions react with the oxygen atoms of the ceramic material (metal (I)) with formation of a mixed oxide (metal (I)+(II)). This thermochemical reaction only takes place if the reaction chamber was evacuated beforehand in the sense of step (a) of the method according to the invention. Preferably the ion implantation takes place in the plasma. Especially preferably, the ion implantation is a plasma-immersion ion implantation (PIII).

The steps combined in this particular manner make the thermochemical reaction of pure titanium and oxide ceramic as solid body possible for the first time, so that a monolithic ceramic body with a mixed-oxide marginal region and metallic surface can be created.

In ion implantation methods, ions that are produced from a target are accelerated in a directional electric field and then impinge on a solid body. The ions penetrate into the body, forming a surface penetration layer. Ion implantation can be influenced by the parameters ion energy and ion dose. The ion energy determines the depth of penetration, and the ion dose determines the number of ions implanted. Using plasma-immersion ion implantation (PIII), the advantages of conventional ion implantation can be transferred to large-area geometries of complex shape. For this, the part to be treated is enveloped—according to the invention, in a high-vacuum chamber—by a plasma generated by a suitable plasma source; by applying negative high-voltage pulses with very short pulse rise times (<microseconds), the more mobile electrons of the plasma are then repelled and the positive ions that remain are accelerated onto the part (implanted). The accelerating voltages are below that of conventional ion implantation (order of magnitude: 30 kV). As the whole area is implanted simultaneously, this method is extraordinarily productive precisely with the various complex geometric shapes encountered in medicine.

In keeping with the desired properties of the monolithic ceramic body according to the invention with mixed-oxide marginal region and metallic surface, all metals and alloys suitable for this can be used as target materials. These are submitted to high-energy vaporization with a magnetron, laser, or any other suitable method, to produce a high "vapor concentration" in the high-vacuum chamber. Suitable target materials comprise metals with high affinity for oxygen. The target materials preferably comprise Ti, Nb, Ta, alloys or compounds thereof. Preferred materials are titanium, a titanium compound or a titanium alloy, wherein the titanium compound is a compound of titanium with elements of the 14th (e.g. C, Si, Ge, Sn, Pb), 15th (e.g. N, P, As, Sb, Bi) or 16th (e.g. O, S, Se, Te, Po) group of the periodic table or a mixture thereof. Elemental titanium and its alloys/compounds are especially preferred, and elemental titanium is quite especially preferred.

According to the invention, for the thermochemical reaction to take place in the marginal region, ion implantation or plasma-immersion ion implantation is carried out with an ion dose from $10^{15}$ to $10^{16}$ ions/cm$^2$ and an ion energy from 1 keV to 2.3 MeV, preferably 1 MeV to 2.3 MeV, indispensably in combination with high vacuum. The temperature is between room temperature and 400° C., especially preferably 350° C. and below. The pressure is about $10^{-3}$ to about $10^{-7}$ mbar, especially preferably under the atmosphere of outer space.

The plasma can be generated continuously (cw-plasma) or pulsed. The properties of the marginal zone, i.e. of the resultant mixed-oxide marginal region and the resultant metallic surface, can be adjusted by means of the plasma parameters, such as the plasma pulse or the energy of the plasma pulse. Either a cw-plasma or a pulsed plasma can be used according to the invention. A combination of the two types of plasma generation is also possible. Preferably, in step (c) a cw-plasma is used, which toward the end of the reaction process can change to pulsed.

The inventors found, surprisingly, that the phenomena of ion-material interaction accompanying conventional ion implantation, such as radiation damage, interactions of defects, amorphization, crystallization, segregation, which make a thermal posttreatment (tempering) necessary, do not occur. The goal of the ion implantation technique used until now for the production of dental implants based on a titanium main body and a ceramic coating was to reduce the affinity of titanium for oxygen during ceramic coating (L. Wehnert, A. Moormann and W. Freesmeyer, Simulation calculations relate to the thermodynamics of the conventional titanium-ceramic bond and the influence of the bond-improving ion implantation technique, Quintessenz Zahntech 1998, Vol. 24, p. 1027-1037). In the present invention, however, the high affinity of metal (II) for oxygen is utilized. The inventors assume that the implanted metal ions (II) react, owing to the high affinity for oxygen, with the oxygen of the ceramic with formation of a complex atomic bond. The marginal region of the unfinished ceramic body is as a result modified chemically into a marginal zone, i.e. a mixed oxide of metal (I) and (II) is formed, and a metallic surface of metal (II) is produced on the mixed-oxide marginal region, so that the aforementioned problems of conventional ion implantation are avoided and subsequent tempering is no longer required. Damage of the ceramic by the processes is avoided completely, in particular also by the choice of relatively low temperature, and a monolithic ceramic is formed with mixed-oxide marginal region and metallic surface, and not a coated ceramic. The absence of phases and phase boundaries clarifies the difference from a coating, and consequently the ceramic body created is a monolith and not a coated ceramic. The previously unsolved layer adhesion problems are thus solved.

As a result of the thermochemical treatment in the sense of step (c), under high vacuum, high-energy metal (II) ions (e.g. titanium ions) penetrate into the marginal region of the unfinished ceramic body, where they form, with the oxygen of the metal (I) oxide (e.g. zirconium oxide) a complex metal (I)-metal (II) oxide (e.g. titanium-zirconium-oxide) and additionally a metallic surface of metal (II). They therefore bring about a chemical reaction and convert the unfinished ceramic body in its marginal region into a marginal zone, so that in the latter the metal (I) (e.g. zirconium) and oxygen combine at the atomic level with the metal (II) atoms (e.g. titanium atoms, titanium ions) and in addition a metallic surface is formed from metal (II). Accordingly, the complex metal (I)-metal (II) oxide with its metallic surface does not form a coating, but represents a chemical transformation of the marginal region of the unfinished ceramic body. The core of the ceramic body and its marginal zone therefore form a monolithic structure, which ends in the metallic metal (II) surface. The concentration of the first metal (I) and of the other metal (II) in the marginal region of the ceramic body according to the invention is ideally, in the middle of the mixed-oxide marginal region of (I) and (II), 50/50%.

In a simplified formulation, it can be said that the thermochemical reaction converts the unfinished ceramic body into a new monolithic body without phase boundaries (ceramic in the core, mixed oxide in between, and titanium on the outside). The thickness can be controlled and adjusted as required and depending on the application.

In one embodiment according to the invention, the ceramic body with the mixed-oxide marginal region and metallic surface can be further coated with one or more metals, especially the other metal (II). The coating with one or more metals is carried out by methods for coating metals or ceramics that are known by a person skilled in the art and are usual in the prior art.

In another embodiment, the coating of one or more metals can be thermochemically nitrided, borided, carburized, nitrocarburized, etc. Of course, the metallic surface of the monolith of metal (II) can also be nitrided, borided, carburized, nitrocarburized, etc. without further coating, if required (surfaces of joints). This leads to hardening of the metallic surface of the ceramic body and is performed for example by plasma-assisted thermochemical nitriding, boriding, carburizing, nitrocarburizing, etc.

In another embodiment according to the invention, the surface of the ceramic body with a mixed-oxide marginal region and metallic surface can be coated with a biocompatible/bioactive material described above. Coating with the biocompatible/bioactive material also takes place in this case by methods for coating ceramics or metals that are known by a person skilled in the art and are usual in the prior art.

The present invention also relates to the use of the ceramic body with a mixed-oxide marginal region and metallic surface as medical implant, especially as tooth implant. Implants can be provided, depending on the application, completely or only partially with a mixed-oxide marginal region and metallic surface. "Partially" is to be understood as meaning that the implant regions that are in contact with bone have a mixed-oxide marginal region and a metallic surface sufficient to ensure definite osseointegration.

"Medical" in the sense of the invention relates to the areas of human medicine, including dentistry, and veterinary medicine, including the dental area. A medical implant in the sense of the invention is a medical device that serves as a replacement for biological structures in the human or animal body, or is used in the body for other purposes. Therefore the medical implants in the sense of the invention comprise implants and dental implants for humans and animals. Dental implants, hip implants, epitheses, artificial joints and prostheses are preferred as medical implants.

A prosthesis is an artificial limb, which replaces a missing part of the body (e.g. owing to disease, accident or amputation), whereas an epithesis primarily has a cosmetic function (e.g. such as an artificial eye or ear). Medical implants and especially prostheses can be used for replacing biological structures, such as bones, joints or parts of bones, in almost all regions of the body, e.g. skull, teeth, upper arm and forearm, elbow, thigh and lower leg, hip, toes, fingers, knee, spinal column, etc. However, hearing aids, artificial limbs, replacement joints, and hair prostheses (wigs) and implants for securing them are also covered by medical implants in the sense of the invention. In special embodiments, hearing aids can be integrated in other implants. This also applies to "medicines" or their containers that are implanted in the body (e.g. heart pacemakers, insulin pumps, etc.).

In some embodiments according to the invention, implants and dental implants are one-part or multi-part implants.

In a preferred embodiment of the invention, only the region of the ceramic body that comes in contact with the bone has a mixed-oxide marginal region with metallic surface (completely or partially). In another embodiment, additionally the region has a mixed-oxide marginal region with metallic surface, which comes in contact with the second part of a two-part implant.

A tooth implant is in particular a one-, two- or multi-part implant and can comprise a screw thread. Preferably the tooth implant comprises an anchoring part, for anchoring the implant in the bone, and a securing part for receiving the superstructure, wherein only the anchoring part has a mixed-oxide marginal region. In a special embodiment of the two-part implant, the region of the ceramic body that comes in contact with the other region (e.g. the abutment on its contact surface between the implant and the abutment) has a partial mixed-oxide marginal region with metallic surface. In this case no screwed connection is required between the two parts, as an optimal accuracy of fit can be achieved, which leads to good seating and high stability of the joint (press-fit). If a screw is made for a multi-part implant according to the invention (e.g. abutments screwed to the implant), either the whole screw, or also only the thread region can have a mixed-oxide marginal region with metallic surface.

In cases when the implant is multi-part, either only one part or both parts in the contact region of the two parts can have a mixed-oxide marginal region with metallic surface. An example of such an embodiment is an artificial hip joint. In this case at least one part of the artificial joint can have a mixed-oxide marginal region with metallic surface. For example, as well as the region that connects to the bone, also the region of the hip joint that comes in contact with the head (ball) has a mixed-oxide marginal region with metallic surface. Or, conversely, only the region that comes in contact with the socket has a mixed-oxide marginal region with metallic surface. It is also conceivable to provide both implant parts according to the invention completely with mixed-oxide marginal region and metallic surface, so that the feared splinter effect on fracture of the implant is largely prevented. One advantage would be that a mixed-oxide marginal region with metallic surface prevents the squeaking or undesirable sound that may arise during movement of the joints. In particular a mixed-oxide marginal region with metallic surface in the head region of an artificial hip joint can prevent squeaking sounds and serves as a "lubricant".

The monolithic ceramic bodies according to the invention with mixed-oxide marginal region and metallic surface can in some embodiments comprise an additional diamond-like carbon layer (DLC) (e.g. on surfaces of joints).

DLC is an extremely hard amorphous carbon layer. In some embodiments the composition can comprise one or more further metal layers, such as gold, silver, platinum, aluminum, copper, iron, nickel, tin, tantalum, zinc and/or chromium, and/or alloys, such as steel or bronze.

DESCRIPTION OF THE FIGURES

FIG. 8: shows an EDX diagram relating to the ceramic body from FIG. 7. It shows the concentration variations of metals (I) and (II) in the mixed-oxide marginal region. The concentration of the respective metal is plotted on the y-axis beginning at 0% and increasing toward the top edge of the diagram. The depth coordinate extending toward the core of the ceramic body is plotted on the x-axis, wherein the abscissa value x=0 lies in the transition region between the mixed-oxide marginal region and the metallic surface;

curve 1 (zirconia-alumina) shows the metal (I) concentration, which runs in the direction of the surface (toward the left) to 0%;

curve 2 (titanium) shows the metal (II) concentration, which runs in the direction of the core to 0%;

The tent-shaped structure resulting from the two curves shows the desirable effect of the concentrations of 50/50% of metals (I)/(II) in the middle of the mixed-oxide marginal region. It can be seen that the two curves run uniformly toward each other in the direction of the middle of the mixed-oxide marginal region and diverge uniformly away from the middle of the mixed-oxide marginal region.

The invention claimed is:

1. A monolithic ceramic body with a mixed-oxide marginal region and a metallic surface;
wherein the ceramic body has a core of an oxide of a first metal (I) and a marginal zone, the marginal zone comprising a mixed-oxide marginal region, which comprises the oxide of the first metal (I) and an oxide of another metal (II), which has an affinity for oxygen, and a metallic surface of metal (II) on the mixed-oxide marginal region;
wherein the marginal zone has been formed by altering the chemical composition of a marginal region of an unfinished ceramic body by means of an activation of the marginal region by shifting the atoms of the marginal region to an energetically excited state and a subsequent thermochemical treatment each under a negative pressure that is $10^{-3}$ mbar or less, and wherein the altering of the chemical composition results in an incorporation of ions of the metal (II) into the lattice of the ceramic material of the ceramic body and also results in a reaction between oxygen atoms of the oxide of the first metal (I) and ions of the other metal (II);
wherein the thermochemical treatment has been induced by ion implantation;
wherein the mixed-oxide marginal region
has a continuous concentration gradient of the first metal (I), starting from 100% in the core to 0% in the transition region to the metallic surface of the ceramic body, relative to the total metal content (I+II); and
has a continuous concentration gradient of the other metal (II), starting from 0% in the core to 100% in the transition region to the metallic surface of the ceramic body, relative to the total metal content (I+II);
wherein the oxygen concentration of the mixed-oxide marginal region remains constant; and
wherein the monolithic structure of the ceramic body is formed without phase boundaries.

2. The ceramic body as claimed in claim 1, in which the first metal (I) is selected from aluminum, zirconium, yttrium, niobium, hafnium, silicon, magnesium, cerium, and mixtures thereof.

3. The ceramic body as claimed in claim 2, in which the oxide of the first metal (I) is zirconia or alumina or a zirconia-alumina mixture.

4. The ceramic body as claimed in claim 1, in which the other metal (II) is biocompatible.

5. The ceramic body as claimed in claim 4, in which the biocompatible metal (II) is titanium.

6. The ceramic body as claimed in claim 5, in which the mixed-oxide marginal region is formed by a titanium-zirconia mixed oxide, titanium-alumina mixed oxide or titanium-alumina-zirconia mixed oxide, and the metallic surface consists of pure titanium.

7. The ceramic body as claimed in claim 1, wherein the mixed-oxide marginal region and the metallic surface thereon, in combination, define a marginal zone of the ceramic body that is between 0.05 and 140 μm thick.

8. The ceramic body as claimed in claim 1, which further comprises one or more layers of further metals.

9. The ceramic body as claimed in claim 1, which additionally comprises one or more biocompatible and/or bioactive coatings.

10. A method of producing a ceramic body with a mixed-oxide marginal region and with a metallic surface as claimed in claim 1, which comprises the following steps to be carried out in a thermochemical reaction chamber on an unfinished ceramic body with a marginal region:
(a) evacuating the reaction chamber to a negative pressure that is $10^{-3}$ mbar or less;
(b) activating the marginal region of the unfinished ceramic body; and
(c) thermochemically treating the marginal region of the unfinished ceramic body.

11. The method as claimed in claim 10, wherein the surface activation in step (b) takes place by a plasma treatment.

12. The method as claimed in claim 10, wherein in step (c) the thermochemical treatment is induced by ion implantation.

13. The method as claimed in claim 12, wherein the ion implantation is a plasma-immersion ion implantation.

14. The method as claimed in claim 12, wherein the ion dose is $10^{15}$ to $10^{16}$ ions/cm$^2$ and the ion energy is 1 keV to 2.3 MeV.

15. The method as claimed in claim 10, wherein step (c) is carried out at a temperature from 20 to 400° C.

16. The method as claimed in claim 10, wherein the method further comprises an additional step (d) of coating the surface of the ceramic body with one or more metals, especially metal (II).

17. The method as claimed in claim 10, wherein the method further comprises a step (e) of coating the surface of the ceramic body with a biocompatible and/or bioactive material.

18. The method as claimed in claim 10, wherein the mixed-oxide marginal region with metallic surface is only formed in a partial region of the unfinished ceramic body.

19. The method as claimed in claim 10, wherein the method comprises an additional step (d) of coating the surface of the ceramic body with one or more metals.

20. A method of producing a ceramic body with a mixed-oxide marginal region with metallic surface as claimed in claim 1, comprising the following steps:
(a) placing an unfinished ceramic body with a marginal region in a thermochemical reaction chamber;
(b) evacuating the thermochemical reaction chamber to a negative pressure that is $10^{-3}$ mbar or less,
(c) activating the marginal region of the unfinished ceramic body under the negative pressure generated in step (b) by shifting the atoms of the marginal region to an energetically excited state, and
(d) altering the chemical composition of the marginal region of the unfinished ceramic body by means of a thermochemical treatment under the negative pressure generated in step (b) in such manner that the marginal region is chemically transformed into a marginal zone of the finished ceramic body, the marginal zone comprising the metallic surface and the mixed-oxide marginal region thereunder which begins underneath the metallic surface, wherein the altering of the chemical composition results in an incorporation of ions of the metal (II) into the lattice of the ceramic material of the ceramic body and also results in a reaction between oxygen atoms of the oxide of the first metal (I) and ions of the other metal (II).

21. The method as claimed in claim 20, wherein the thermochemical treatment is induced by ion implantation having an ion dose from $10^{15}$ to $10^{16}$ ions/cm$^2$ and an ion energy of up to 2.3 MeV.

* * * * *